(12) United States Patent
Smither

(10) Patent No.: US 7,468,516 B2
(45) Date of Patent: Dec. 23, 2008

(54) HIGH RESOLUTION X-RAY AND GAMMA RAY IMAGING USING DIFFRACTION LENSES WITH MECHANICALLY BENT CRYSTALS

(75) Inventor: Robert K. Smither, Hinsdale, IL (US)

(73) Assignee: UChicago Argonne, LLC, Chicago, IL (US)

( * ) Notice: Subject to any disclaimer, the term of this patent is extended or adjusted under 35 U.S.C. 154(b) by 257 days.

(21) Appl. No.: 11/479,797

(22) Filed: Jun. 30, 2006

(65) Prior Publication Data

US 2008/0001096 A1    Jan. 3, 2008

(51) Int. Cl.
*G21K 1/06*    (2006.01)
(52) U.S. Cl. .......................... 250/393; 378/85
(58) Field of Classification Search ................. 250/393; 378/84, 85
See application file for complete search history.

(56) References Cited

U.S. PATENT DOCUMENTS

| | | | | |
|---|---|---|---|---|
| 2,688,094 A | * | 8/1954 | Dumond | 378/85 |
| 3,032,656 A | * | 5/1962 | Hosemann et al. | 378/84 |
| 4,429,411 A | * | 1/1984 | Smither | 378/84 |
| 4,461,018 A | * | 7/1984 | Ice et al. | 378/84 |
| 4,599,741 A | * | 7/1986 | Wittry | 378/85 |
| 4,882,780 A | * | 11/1989 | Wittry | 378/84 |
| 5,596,620 A | * | 1/1997 | Canistraro et al. | 378/84 |
| 5,787,146 A | * | 7/1998 | Giebeler | 378/82 |
| 5,869,841 A | * | 2/1999 | Smither | 250/505.1 |
| 6,829,327 B1 | * | 12/2004 | Chen | 378/44 |
| 2005/0175148 A1 | * | 8/2005 | Smither | 378/84 |

* cited by examiner

*Primary Examiner*—David P Porta
*Assistant Examiner*—Mark R Gaworecki
(74) *Attorney, Agent, or Firm*—Cherskov & Flaynik

(57) ABSTRACT

A method for high spatial resolution imaging of a plurality of sources of x-ray and gamma-ray radiation is provided. High quality mechanically bent diffracting crystals of 0.1 mm radial width are used for focusing the radiation and directing the radiation to an array of detectors which is used for analyzing their addition to collect data as to the location of the source of radiation. A computer is used for converting the data to an image. The invention also provides for the use of a multi-component high resolution detector array and for narrow source and detector apertures.

13 Claims, 14 Drawing Sheets

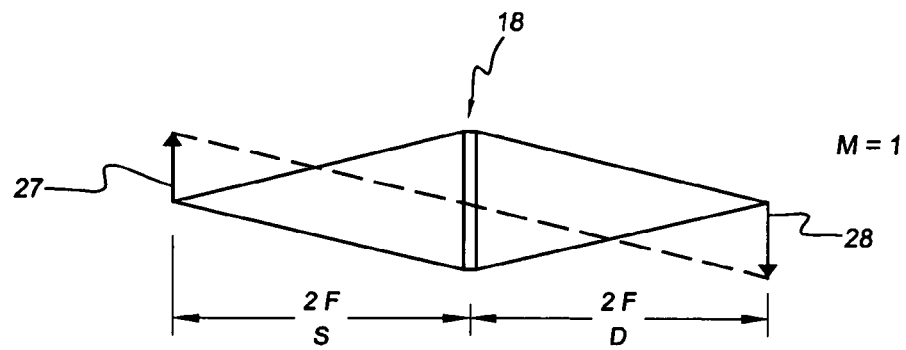
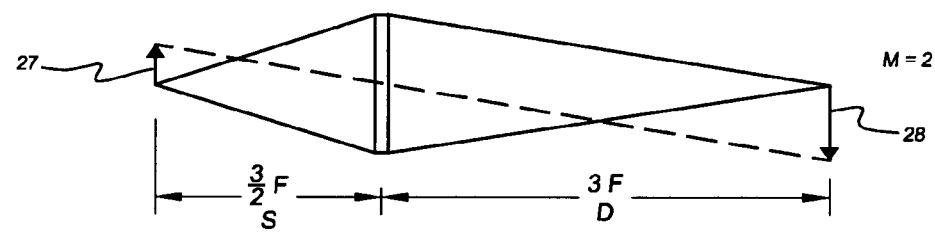
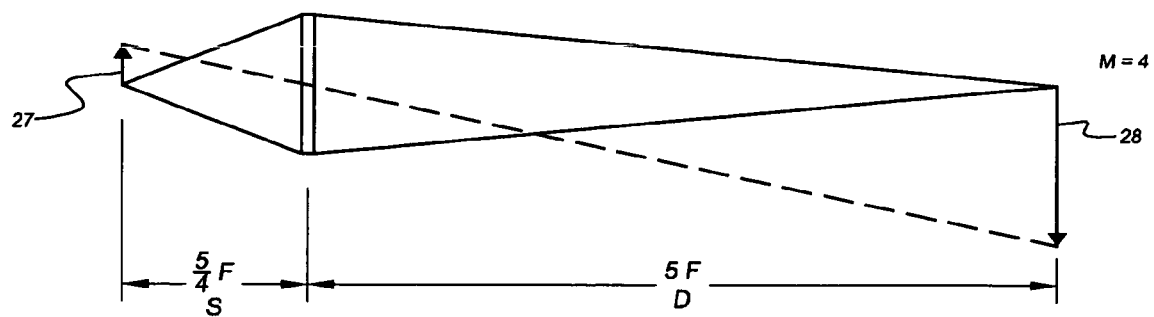
*Fig. 3b*

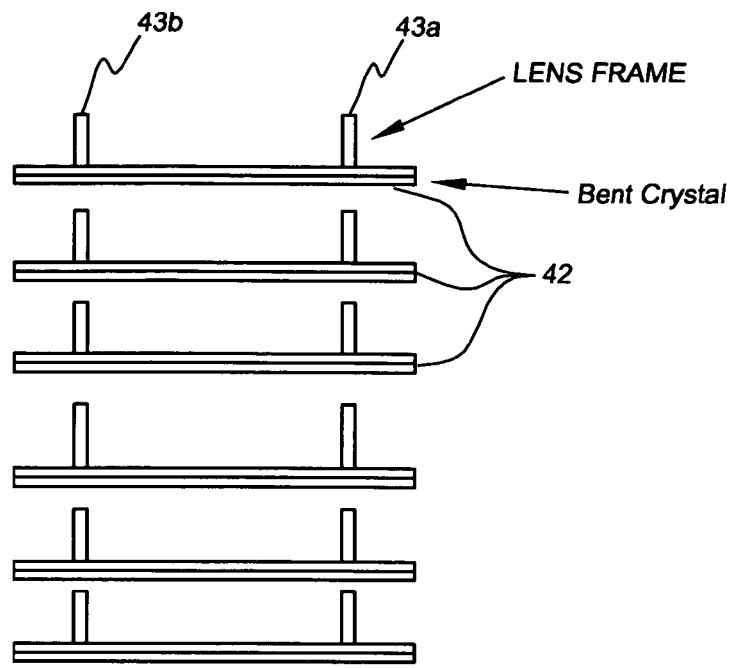
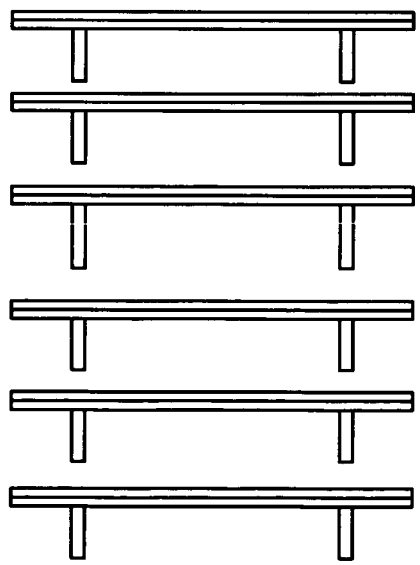
Side view of medical imaging lens
*Fig. 10*

Crystal support ring and mounted crystal

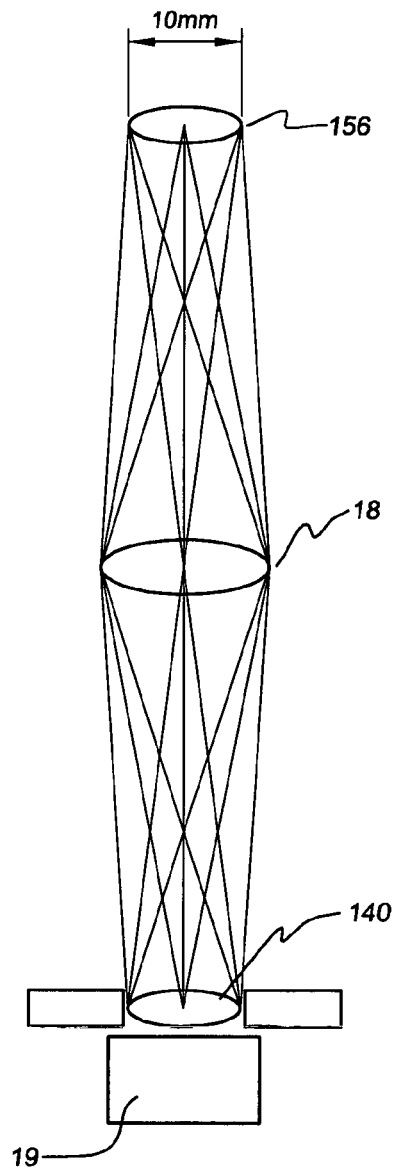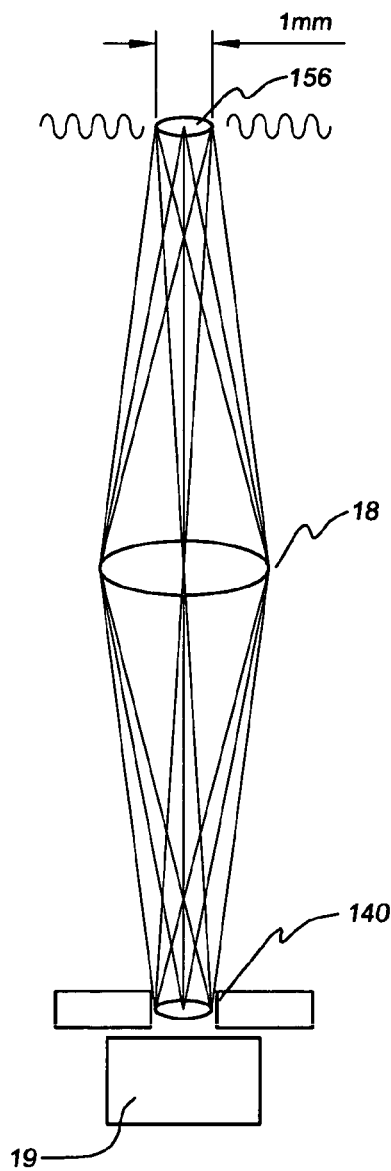
*Fig. 12a*  *Fig. 12b*

HIGH RESOLUTION X-RAY AND GAMMA RAY IMAGING USING DIFFRACTION LENSES WITH MECHANICALLY BENT CRYSTALS

CONTRACTUAL ORIGIN OF INVENTION

The United States Government has rights to this invention pursuant to Contract No. W-31-109-ENG-38 between the U.S. Department of Energy and the University of Chicago, representing Argonne National Laboratory.

BACKGROUND OF THE INVENTION

1. Field of the Invention

This invention relates to a method for improving the imaging of a source of radiation and to a device for imaging a source of radiation, and more specifically, this invention relates to a method and device for producing a high spatial resolution three-dimensional image of a source of x-ray and gamma-ray radiation for medical and other applications by using a plurality of nearly perfect mechanically bent diffracting crystals which focus x-ray and gamma-ray radiation onto one or more detection devices.

2. Background of the Invention

Cancer tumor cells have high rates of metabolism and multiply rapidly. Substances injected into the body tend to migrate to locations of such high growth and become incorporated in this new growth. If the injected substance is a short-lived radioactive isotope, the location of a tumor can be detected by locating the region of high radioactivity. Aside from pinpointing tumor location, an image of the tumor is also desirable to ascertain its shape, size, and juxtaposition with adjacent structures. For many medical applications it is imperative that a tumor be detected as early as possible, and early tumors are very small in size. Thus their detection and identification requires the ability to image very small sources. Also, medical research often uses small animals, with very small organs, and the availability of devices with very high spatial resolution is of the utmost importance.

One method used to detect tumors is to first inject a body with radioactive compounds such as the Technetium isotope $^{99m}Tc$, which is a 140.5 kiloelectron volt (keV) gamma emitter having a half-life of 5.9 hours. The gamma rays are detected by a large sodium iodide (NaI) scintillator crystal placed behind a collimator grid yielding at best an 8 millimeter (mm) resolution at the location of the source. The scintillator is viewed by a plurality of photomultiplier tubes and the location of a scintillation event is determined by a computer analysis of the relative intensity of the photomultiplier signals. The collimator/scintillator assembly is placed above and very close to the patient. Aside from this method yielding a low resolution of between approximately 8 mm and 1 centimeter (cm), the image produced is limited to the plane parallel to the surface of the scintillator. As such, the technique provides no depth information about the source. This deficiency can be remedied somewhat by adding another collimator/scintillator assembly below the patient, comparing the counting rate of the two scintillators, and thus estimating the position of the source along the line joining them. In the latest revision of this method the large NaI detector plus collimator is rotated around the patient, taking a plurality of images at different angles. This allows one to generate a three-dimensional image of the radiation emitting area. There are considerable additional costs associated with this method and the fact that this method has been introduced in spite of the additional costs underscores the importance of three-dimensional imaging.

Another popular imaging technique is positron emission tomography (PET), used in diagnosis and medical research. In PET, a chemical compound containing a short-lived, positron-emitting radioisotope is injected into the body. The positrons (positively charged beta particles) are emitted as the isotope decays. These particles annihilate with electrons in surrounding tissue. Each annihilation simultaneously produces two 511 keV gamma rays traveling in opposite directions. After passing through collimators, these two gamma rays are detected simultaneously by scintillation detectors placed at 180 degrees to each other, and on opposite sides of the patient. The signals from the detectors' photomultiplier tubes are analyzed by a computer to facilitate the production of an image of the radiation-emitting region.

Numerous drawbacks exist with scintillation detector tomography. For instance, the typical coarse resolution of no less than 8 mm often results in smaller structures being overlooked. This prevents early detection of cancerous tumors when they are least likely to have metastasized and when treatment is most likely to succeed. This is especially a disadvantage in the detection of breast cancer tumors wherein the tumors often become virulent before growing to a detectable size. Presently, mammography uses x-rays to detect tissue calcification. The assumption is made that this calcification is due to dead cancer cells and that there is a live cancer tumor in the immediate vicinity. Often however, there is no live tumor where calcification has been detected. In fact, the calcification may not have been due to a tumor at all. Unfortunately then, positive mammography results often lead to unnecessary surgical operations.

Also, because poor spatial resolution often causes images of actual small tumors to be diffuse, variations in background radiation are often mistaken for actual tumors, leading to unnecessary surgical operations. This inadvertent incorporation of background radiation is an artifact of scintillation detector use wherein the detector must be large enough to cover a given area of the body. Aside from intercepting the radiation emanating from the source under observation, however, the large detectors also detect all ambient background radiation penetrating the scintillating region and this ambient radiation is analyzed as if it had been emitted by the source under observation.

Another drawback to using imaging techniques incorporating scintillation detectors is that all of the various radiations emitted by the source are detected by the detectors. As such, a specific radiation having an energy indicative of a specific, injected isotope cannot be easily scrutinized.

Lastly, because collimators allow for the detection of only the radiation that is emitted in a very narrow direction in space, the patient has to be injected with a relatively large amount of radioactive material.

Recently, efforts have been made to improve scintillation detector tomography. Some PET instruments now achieve a resolution as small as 4 mm. Such improvements entail considerable expenditures and have the additional drawback that the improvement in resolution has come at the cost of a decrease in counting rate. This entails in turn either a longer examination time per patient or the injection of a stronger dose of radiation. Furthermore, the prospects for further improvements in resolution are limited by the fact that such improvements require collimators with ever smaller apertures, and therefore greater mass, together with lower count rates. This increase in collimator mass will increase the number of forward Compton-scattered photons in the collimators and these forward scattered photons are often indistinguishable from those emanating directly from the source.

Significant improvements in spatial resolution and in detection efficiency as well as a three dimensional location of the source using a crystal diffraction method for focusing the radiation emanating from the source was disclosed in U.S. Pat. No. 5,869,841 (1999) (granted to the same inventor as the present invention and assigned to the same assignee) and incorporated herein by reference. Because of the focusing of the radiation emitted by the source, one requires the injection of much smaller amounts of radioactive substances at a site on the patient's body in order to locate features of interest. Experiments at the inventor's laboratory have demonstrated the effectiveness of this method and have achieved a spatial resolution of 7 mm. Modification of this crystal diffraction lens imaging system lead to improvements in the resolution, achieving a spatial resolution of 3.2 mm full width half maximum (FWHM), but with a reduction in sensitivity (counting rate). While this is adequate under many circumstances, and better than most present systems for imaging radioactive sources better spatial resolution with better sensitivity would provide significant advantages. U.S. Pat. No. 5,869,841 taught the use of diffracting crystals whose acceptance angle was increased by principally by means of a mosaic structure in the crystal possibly supplemented by bending the crystal.

Thus a need exists in the art for an improved method and device for imaging x-ray and gamma-ray sources with sufficient spatial resolution, so as to obtain better sensitivity, to accurately observe and image structures smaller than 7 mm in size, even down to 0.3 mm in size or less. The invented method and the resulting device must have sufficient energy resolution to allow the imaging of radiation of a selected energy to the exclusion of others. The method and device also must limit the radiation to which the patient is exposed by incorporating a redirecting or "focusing" mechanism to detect radiation emanating from a tumor while disregarding ambient levels of radiation.

SUMMARY OF THE INVENTION

It is an object of the present invention to provide a method and a device for high spatial resolution imaging sources of gamma-ray and x-ray radiation that overcome many of the disadvantages of the prior art.

Another object of the present invention is to provide a small bulk device using crystal diffraction imaging of sources of gamma and x-ray radiation that features high detection efficiency. A feature of the present invention is the use of a plurality of non-coplanar assemblies each comprising one or more crystal diffraction lenses comprising nearly perfect mechanically bent crystals. An advantage of the invention is a much higher efficiency for the diffraction lenses. Another advantage of this invention is that the diffraction lenses can be made much smaller in diameter and with much shorter focal lengths.

Still another object of the present invention is to provide a method for producing a high spatial resolution image of a radiation source located in a patient. A feature of the invention is the use of high purity and high quality mechanically bent diffracting crystals. An advantage of the invention is the ability to image sources as small as 0.3 mm into images of comparable size.

A further object of the present invention is to provide a method for producing crystal diffraction lenses with short focal lengths. A feature of the present invention is that the spatial resolution of the system is not limited by the angle subtended by the radial thickness of a crystal element. An advantage of the present invention is that one can use shorter source-lens distances than heretofore without loss of sensitivity and resolution and thus obtain efficient shorter focal length system.

Yet another object of the present invention is to provide a radiation imaging method that produces a magnified image of a radiation source located inside a patient. A feature of the invention is the ability to manufacture small size lenses with a short positive focal length. An advantage of this invention is the ability to produce an image with a magnification of at least a factor of four.

In brief the present invention provides a method and a device for high spatial resolution imaging of sources of x-ray and gamma radiation comprising supplying one or more sources of radiation; focusing said radiation onto one or more detectors by means of mechanically bent nearly perfect diffracting crystals; analyzing said focused radiation to collect data as to the type and location of the sources of the radiation; and producing an image using the data. The invented device features lenses of short focal length that can produce images with a magnification by at least a factor factor of four. Also, the present invention provides a method for manufacturing mechanically bent crystals for use in high spatial resolution diffraction lenses and other applications. The method comprises: a) selecting a crystalline material and cutting from large single crystals single crystal slabs of desired thickness and with Miller indices orientation determined according to the radiation to be observed; b) forming sets of two or more juxtaposed plates, at least one of which plates is one of said crystal slabs, by contacting said plates with an uniform layer of glue that hardens only when it is activated; c) bending to a predetermined curvature one or more of said sets by means of a bending apparatus that allows in-situ measurements of the curvature of the plates; d) activating said glue while the set of plates is in the bending apparatus; and e) releasing said set from the bending apparatus.

BRIEF DESCRIPTION OF THE DRAWING

The present invention together with the above and other objects and advantages may best be understood from the following detailed description of the embodiment of the invention illustrated in the drawing, wherein:

FIG. 3*b* is a series of schematic views of lens/detector assemblies with different magnification, in accordance with features of the present invention;

FIG. 10 is a schematic profile cross sectional view of a lens/detector assembly as shown in FIG. 9, taken along lines 10-10, of an embodiment of a crystal diffraction lens, in accordance with features of the present invention;

FIG. 12a illustrates the effect of a large aperture in front of the detector array in accordance with features of the present invention;

FIG. 12b illustrates the effect of a narrow aperture in front of the detector array in accordance with features of the present invention;

DETAILED DESCRIPTION OF THE INVENTION

The present invention improves the imaging of sources of x-ray and gamma-ray radiation. The present invention provides a method and a device for high spatial resolution imaging of a source of radiation comprising using high purity and high quality mechanically bent diffracting crystals. Also, the present invention provides a method for manufacturing mechanically bent crystals for use in high spatial resolution diffraction lenses and other applications. The invented method can yield a detected image as small as 0.3 mm (Full Width at Half Maximum (FWHM) for a point source). Also, this invention provides the ability to produce an image with a magnification of at least a factor of four.

Figure 1:
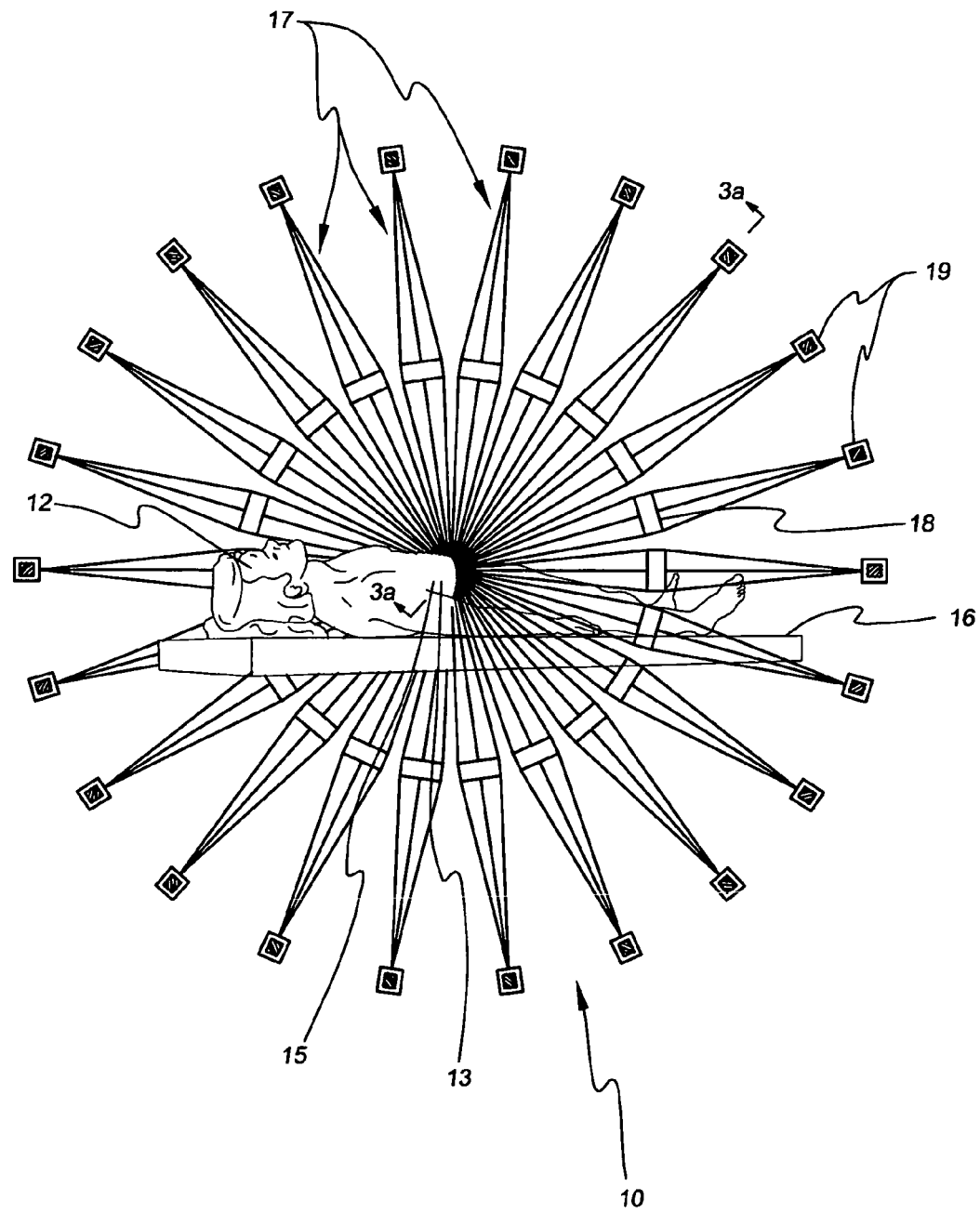
FIG. 1 is an elevational view of a single coplanar array of lens/detector assemblies in accordance with features of the present invention.

The invented method results in a device, designated generally as numeral 10 in FIG. 1, that incorporates a plurality of lens/detector assemblies 17 to first focus and then detect radiation emanating from a radioactive source 15, such as a tumor 13 in a patient 12 that has incorporated some radioactivity. Each lens/detector assembly 17 comprises a plurality of high efficiency and high resolution crystal diffraction lenses 18 that focus onto detector arrays 19 only the radiation of a desired energy and origin. As disclosed infra, and with reference to FIG. 9, each lens 18 comprises a plurality of concentric rings 45, which in turn are comprised of very accurately mounted and bent perfect or nearly perfect diffracting crystals. These crystals are oriented with their principal radius of curvature in the same plane as the radiation, so that only radiation having a predetermined energy is focused onto a detector array 19. The detector arrays 19 of the device are shielded from unwanted radiation.

The device 10 is designed to accommodate the detection of radiation from a myriad of sources. For clarity, the radiation source 15 in the exemplary embodiment shown in FIG. 1 is a tumor or other tissue that has absorbed a radio-isotope in vivo, whereby the tumor emits radiation of a predetermined wave length $\lambda$. However, other radiation sources are also appropriate, including radioisotope-impregnated fissures in a mineral or in a manufactured object, an x-ray or gamma-ray beam scattering from a target, x-rays or gamma rays produced by particle-beam bombardment of a target or emanating from either a terrestrial or astrophysical source.

After emanating from the source 15, the radiation is focused by the diffraction lens 18. The lens 18 directs the radiation to a detector array 19. The output of the detector array is analyzed by a computer. The exemplary device 10 is a plane circular array of lens/detector assemblies 17 with the source 15 situated at the center 13 of the array, the detector arrays 19 positioned along the periphery of the array, and the focusing means 18 positioned approximately medially between the source 15 and the detector assemblies 19. As noted supra, the detector arrays 19 define the periphery of the plane circular array and therefore are distally placed relative to the center 13 of the circular array and the focusing lens 18.

Figure 2:
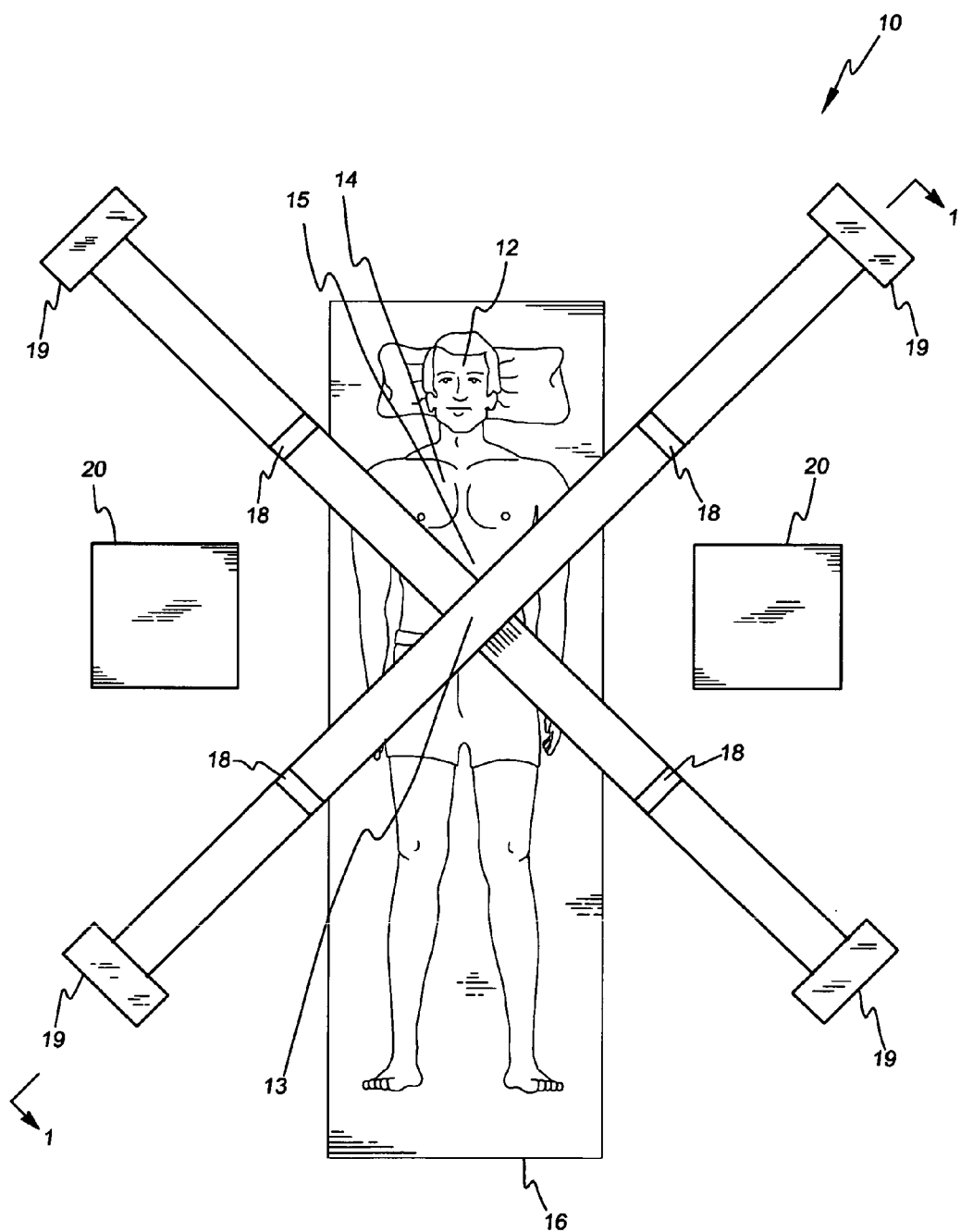
FIG. 2 is a cross-sectional, plan view of two intersecting arrays of lens/detector assemblies, in accordance with features of the present invention.

A three-dimensional scan of the source 15 can be accomplished with two lens/detector assemblies 17. FIG. 2 is an exemplary embodiment of a three-dimensional imaging system comprising two intersecting and concentric orthogonal arrays 10 of the lens/detector assemblies. The radiation source 15, resting on a movable platform 16, is located at the intersection of the two arrays at their common center 13 at the time of imaging. Prior to high resolution imaging operations, conventional scintillation counters 20 are provided for quick scan features of the radiating area to approximately locate the source's position. For the sake of additional clarity, FIG. 1 is an elevational view of FIG. 2 taken along lines 1-1.

If the present invention is used as a medical imaging system, then the source 15 is a patient in whom a radioisotope has been injected. A reference source 14 of the same isotope is positioned at a suitable point on the patient's body and the location of the patient's tumor is measured with respect to the reference source 14. Imaging of an extended source is best accomplished by moving the movable platform 16 across the center 13 of the intersecting arrays 10. Alternatively, one could move the lens system relative to the source if means have been provided therefore.

The positions of the lenses, detectors, and a platform 16 containing the source 15 and the reference source 14 are monitored by conventional electronic sensors (not shown) and recorded and analyzed by a computer (not shown).

Lens/Detector Assembly Detail

Each lens/detector assembly 17 incorporates a plurality of movable focusing lenses 18 and detector arrays 19. The positions of the lenses, detectors and a platform 16 containing the source 15 are monitored by conventional electronic sensors (not shown) and recorded and analyzed by computer (not shown).

Figure 3A:
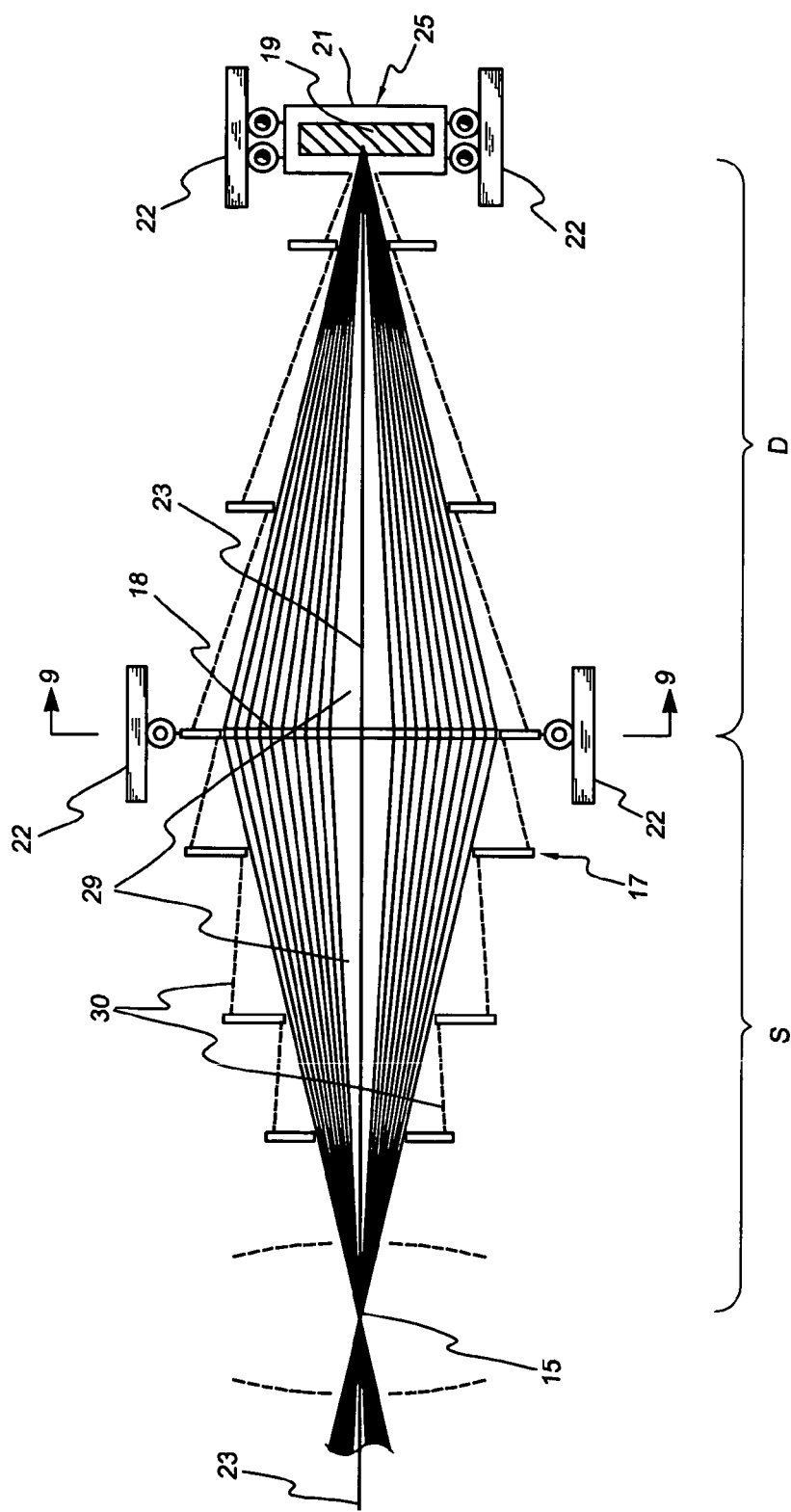
FIG. 3*a* is a cross sectional view of a lens/detector assembly as shown in FIG. 1, taken along lines 3*a*-3*a*, in accordance with features of the present invention.

FIG. 3a is a cross sectional view of FIG. 1 taken along lines 3a-3a and presents a detailed depiction of the lens/detector assembly 17. Each lens/detector assembly 17 incorporates a plurality of movable diffraction lenses 18, detectors 19, and shielding around the detectors 19. Shielding is also placed along the longitudinal axis 23 of the assembly and longitudinally along the outside of the assembly. The axis and outside radiation shields 29, 30 respectively, are cone-shaped and mounted between the lens 18 and the source 15 and the lens and the detector array 19. Generally, the axis and outside shields can be any convenient configuration such as cone- or cylindrically-shaped. Lead, iron, and brass are suitable shielding materials.

In FIG. 3a S and D denote the lens-source, and the lens-detector distances respectively. Lenses and detectors are mounted on tracks 22 equipped with electronic sensors. The tracks allow for independent axial movement of either or both the lens 18 and detector 19. For unit magnification, the detector array is moved in the same direction but twice as far as the lens.

The present invention has the advantage of allowing the production of short focal length, focusing lens systems where the distance from the source to the lens is smaller than the distance from the lens to the detector, which magnifies the size of the image. See FIG. 3b. This in turn allows arrangements where the image is magnified. If F=lens focal length, then 1/F=1/S+1/D and the magnification M=D/S. FIG. 3b illustrates source/lens/detector arrangements with M=1, 2, and 4 respectively, with a source dimension being 27 and the corresponding image dimension 28. Note that for M=1 the total source/detector distance is 4F and for M=4 it is 6.25F, thus the importance of having a short F.

A presently available copper lens as disclosed in U.S. Pat. No. 5,869,841 (1999) has a focal length of 50 cm and a distance from source to detector of 200 cm. A magnification of a factor of 2 would increase this source to detector distance to 225 cm and a magnification of a factor of 4, would increase the source to detector distance to 312.5 cm, which is very difficult to handle. A reduction in the focal length of the lens by a factor of 4 would reduce this source to detector distance to 56.3 cm.

Detector Detail

Generally, the detector array 19 comprises solid state detectors made of silicon or germanium or a composite material such as CdTe or CdZnTe. The detector array may include commercially available pixel detectors. The detectors are mounted a in movable housing 25 (See FIG. 3a). Scintillation detectors may also be used.

A 3 by 3 detector array enables a determination as to whether the source being imaged is on the axis of the lens or off the axis of the lens and if off-axis, to determine in which direction it is off-axis. One may also use a 2 by 2 array, where the source is on axis when the counting rate in all four segments is equal. In the 3 by 3 array, the source is on axis when most of the radiation interacts with the central detector and the other detectors have equally weak count rates. The 3 by 3 array can also be used to obtain the lowest background possible. If the center detector is large enough to intercept all of the focused radiation when the source is on axis, then one can use the off-center detectors to estimate the background in the center detector. Furthermore, an energy sum coincidence can be made between the center detector and the outside detectors that can increase the efficiency for detecting the full energy of the detected photon ray, thus increasing the full energy count rate without increasing the background count rate. Thus in this latter arrangement one has the efficiency of a large detector for detecting the full energy of the gamma ray, while retaining the low background counting rate of only the central detector.

An array comprising a large number of detector elements, or even a pixel detector, can also be used. In general terms, a point source is imaged into a spot equal in size to the cross section of the diffracting crystals in a direction orthogonal to the photon beam in prior art Bragg lens designs or lens designs using mosaic crystals but in the invented lens design using curved crystals, the detector image can be smaller than this dimension. Thus the size of an element in a detector array should be equal to or less than the desired spatial resolution. The present invention provides a spatial resolution of 0.3 mm. With a pixel detector array, the present invention allows nearly a one to one correspondence between source and image points, see infra. The size of the source that can be imaged directly on the detector by a single lens without moving the lens is determined by the amount of curvature in the crystal diffraction elements that make up the lens if the radial (orthogonal to the device axis) dimension of the crystal element is small. The larger the total curvature in the crystal element, the larger the area imaged. If the radial size of the crystal element is comparable to the source, then its radial size will also contribute to the imaged area. Once the response function of the lens is measured with a point source, a computer can be used to translate the image measured on a pixel detector to generate the an image of the source.

The Crystal Diffraction Process

Figure 4A:
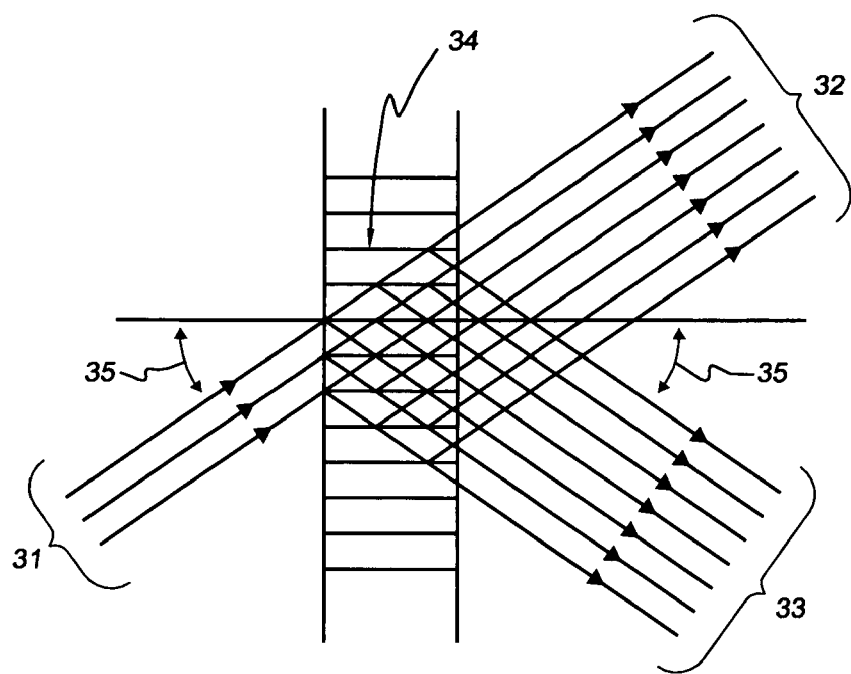
FIG. 4*a* illustrates the phenomenon commonly known as Laue Diffraction.
Figure 4B:
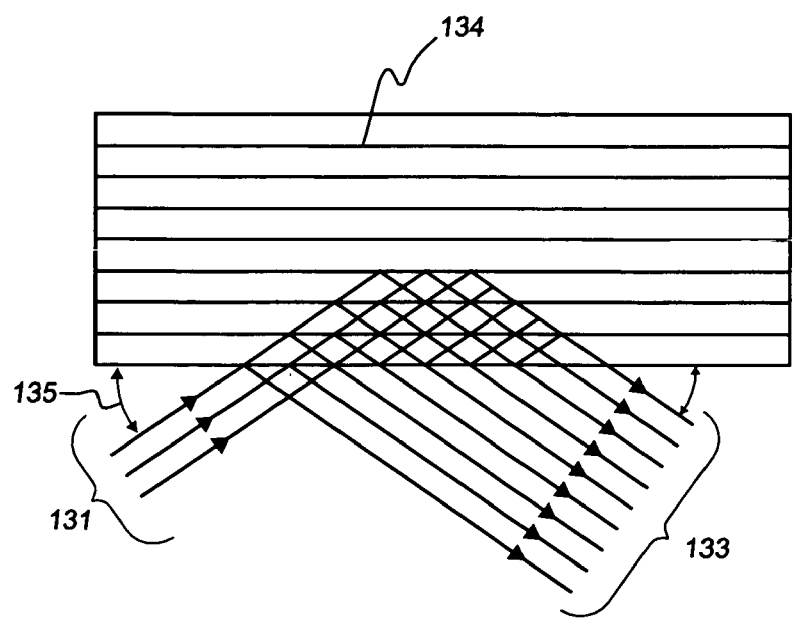
FIG. 4*b* illustrates the phenomenon commonly known as Bragg Diffraction.

In order to focus x-ray and gamma radiation, the present invention utilizes the phenomenon of crystal diffraction which is illustrated in FIGS. 4a and 4b.

FIG. 4a depicts the phenomenon known as Laue diffraction, a volume effect that is most important with higher energy photons. The incident radiation beam 31 enters through one surface of a diffracting crystal. After interacting with a specific array of parallel atomic layers 34, the radiation beam is split into two beams, a transmitted beam 32, and a diffracted beam 33, with both beams exiting through a surface opposite to the one through which the radiation entered. Both the transmitted and the diffracted beams are produced by a coherent superposition of the scattering amplitudes of the radiation scattered by atoms in the parallel crystal layers. The angle 35 between the radiation beam and the crystal layers is designated as p. Typically between $10^4$ and $10^7$ atomic layers are suitable to approach 50% diffraction. The actual number of layers depends on the wavelength of the gamma ray. In practice, the maximum diffracted beam is less than 50% of the incident beam because some absorption of the beam occurs as it passes through the crystal.

FIG. 4b depicts the phenomenon known as Bragg diffraction acting upon an incident beam 131. After multiple scatterings with the atoms comprising a specific array of parallel atomic layers 134 at the surface of the crystal, the net outcome for low energy photons is the emergence of a "diffracted" beam 133, which can contain nearly all of the incident photons. Some absorption of the radiation occurs during this process which continues until either the radiation is diffracted out of the crystal or is absorbed in the crystal. For photon energies similar to those used in medical imaging, the photons penetrate deep into the crystal resulting in an appreciable loss due to absorption. The angle 135 between the radiation beam and the crystal layers is designated as p. The diffracted beam exits through the same surface as the one through which the radiation entered. Again, the beam is produced by a coherent superposition of scatterings by atoms in the parallel crystal layers. Bragg diffraction is a surface phenomenon that is most effective for energies well below 30 keV and the fraction diffracted then can reach 90%.

For both Laue and Bragg diffraction, diffraction occurs only when the Bragg condition is obeyed, (equation 1):

$$\lambda = 2 d_{hkl} \sin p \qquad \text{Eq. 1}$$

where $\lambda$ is the radiation wavelength, $d_{hkl}$ the spacing between the atomic layers indicated by the Miller indices h,k,l, and p the angle between the direction of the radiation beam and the atomic layers (one can convert energy E in keV to wavelength $\lambda$ in Angstrom units by using the relation $\lambda=12.397/E$). With perfectly parallel atomic layers, only rays within a few arc seconds of p will be diffracted (i.e., the "acceptance angle" is only a few seconds of arc), so that one can obtain a large diffraction efficiency only if the rays are nearly parallel, i.e. only if the source is very far away.

Heretofore, several methods have been used to increase the acceptance angle. One method has been to utilize imperfections that are either naturally present or else artificially introduced within the crystal so that all the crystal planes are no longer parallel to each other. Methods previously employed for introducing imperfections include chemical doping, differential heating, stressing, bending beyond the elastic limit when heated and mechanically inducing dislocations. These imperfections in the crystal give rise to a three dimensional mosaic structure. The angle between the rays with the lowest angle p and those with the largest p is the acceptance angle (also known as the "rocking angle" which is the full width at one half maximum of this distribution). Ordinarily, rocking angles of between 100 and 800 arc seconds or larger can be obtained by the above methods. 800 arc sec is adequate for a first scan where a spatial resolution of 4 mm with a source to lens distance of 100 cm. A rocking angle of between 50 and 150 seconds of arc is required when a 1 mm spatial resolution is required. The use of crystals with a smaller rocking angle is not indicated unless other components of the system are adjusted so as to yield a better than 1 mm resolution (e.g. reduction of the sizes of the detectors and the source and detector apertures).

Figure 5:
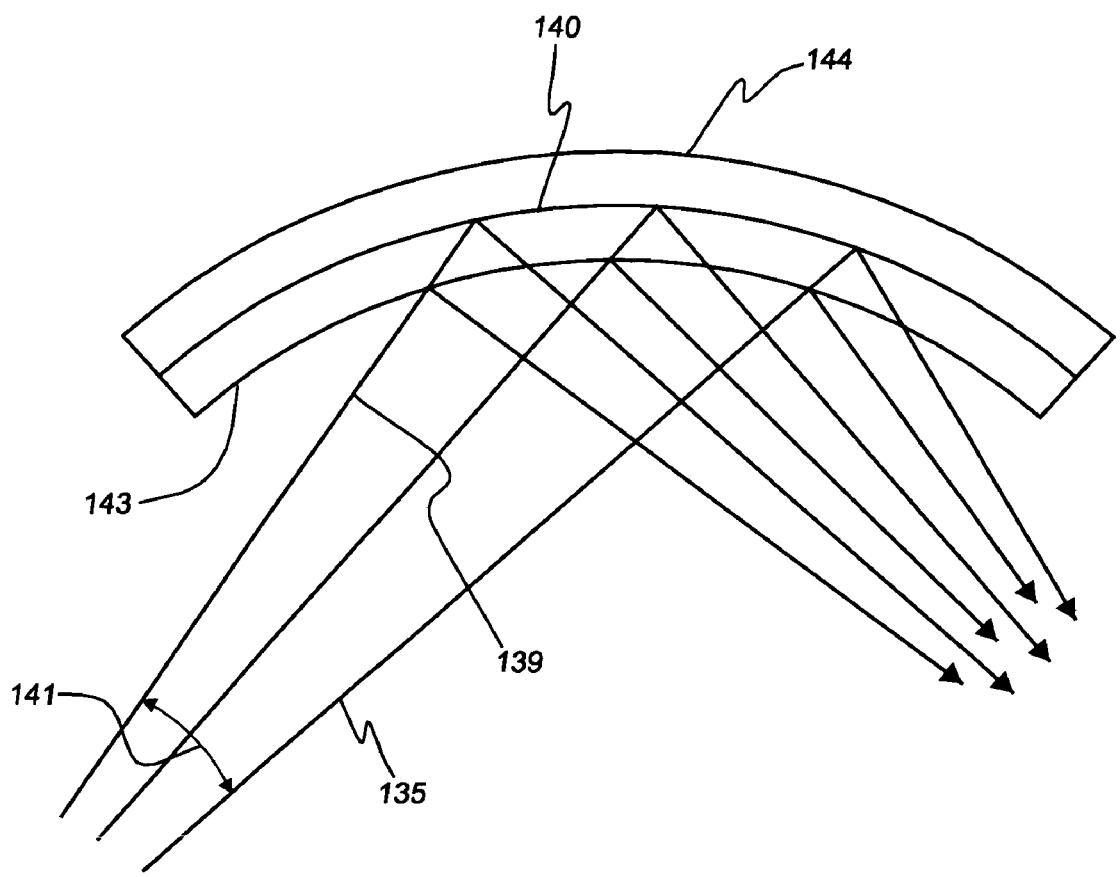
FIG. 5 illustrates the effect of crystal bending in Bragg Diffraction, in accordance with features of the present invention.

FIG. 5 shows that for Bragg diffraction the acceptance angle for monochromatic radiation can be increased if the crystal is curved to form an arc coplanar with the radiation beam. Rays coming at different angles 139 will still find sets of planes 140 where the spacing between planes is such that the Bragg condition is obeyed. (The angle 41 between the rays 135 with the lowest angle p and the rays 139 with the largest p is the acceptance angle.) Thus, in the first place, the curved concave shape of the crystals can produce a significant focusing effect, i.e. an increase in the surface area that reflects radiation onto the detector, as is well known from geometrical optics. Furthermore, the stresses resulting in the bending of the crystal in the focusing geometry produces a lengthening $\Delta l$ of the length l the convex surface of the bent crystal and a shortening or compression of the concave surface. This results in a continuous gradient in the spacing t of the planes parallel to the curved surface. The spacing between planes proximal to the concave face 143 is increased while the spacing between planes proximal to the convex face 144 is decreased. This results in an increase in the radial depth of the crystal from which radiation from the source is diffracted onto the detector. To a first approximation, the increase in the diffracting depth, typically a factor of three, is given by the absolute value of the inverse of what is known as the Poisson ratio P for the set of diffracting planes in question. (P is given by $\Delta t/t)/\Delta l/l$). The two effects (focusing and depth increase) combine to produce an enlarged volume of diffracting scattering centers, and, inasmuch as diffraction is a coherent phenomenon with the diffracted intensity proportional to the square of the number of scatterers, the resulting diffracted intensity with a bent crystal is much larger than that obtainable with an unbent crystal (see FIG. 4b). The fact that the spacing between planes proximal to the concave face 143 is increased while the spacing between planes proximal to the convex face 144 is decreased entails that the Bragg angle is larger for planes near the convex face than for planes near the concave face. While the above discussion is limited to Bragg diffraction, the same considerations apply to the Laue diffraction process.

The Dual Focusing Properties of Bent Crystals.

A bent diffraction crystal focuses gamma rays in two different ways (the following discussion focuses on Laue diffraction). The first method focuses the gamma ray by matching the curvature of the crystal to the opening angle of the incident gamma rays so that the Bragg angle between the incident radiation and the crystalline planes remains constant. This is illustrated in FIG. 5. The gamma ray from a point on the source passes through the crystal until it reaches a region where the Bragg condition is met, at which point it is diffracted, Because the crystal is curved the gamma ray will not encounter a second set of planes in the crystal where the Bragg condition is met so it will emerge from the crystal in the diffracted beam. This effect allows the diffraction efficiency to approach 100 percent. The only loss will be to atomic absorption in the crystal. Each point on the source will use an different part of the crystal to be diffracted. Thus the image of a point source is a narrow line on the detector. This line can be vary narrow approaching the radial width of the region that is generating the diffraction (typically 10 to 100 microns). The corresponding bent crystal on the opposite side of the lens will produce a similar line image. The ideal radius of curvature, r(Bragg), for the bent crystals for this kind of focusing is given by r(Bragg)=S/(sin p) where S is the distance from the source to the lens and sin p is the sine of the Bragg angle.

Figure 6:
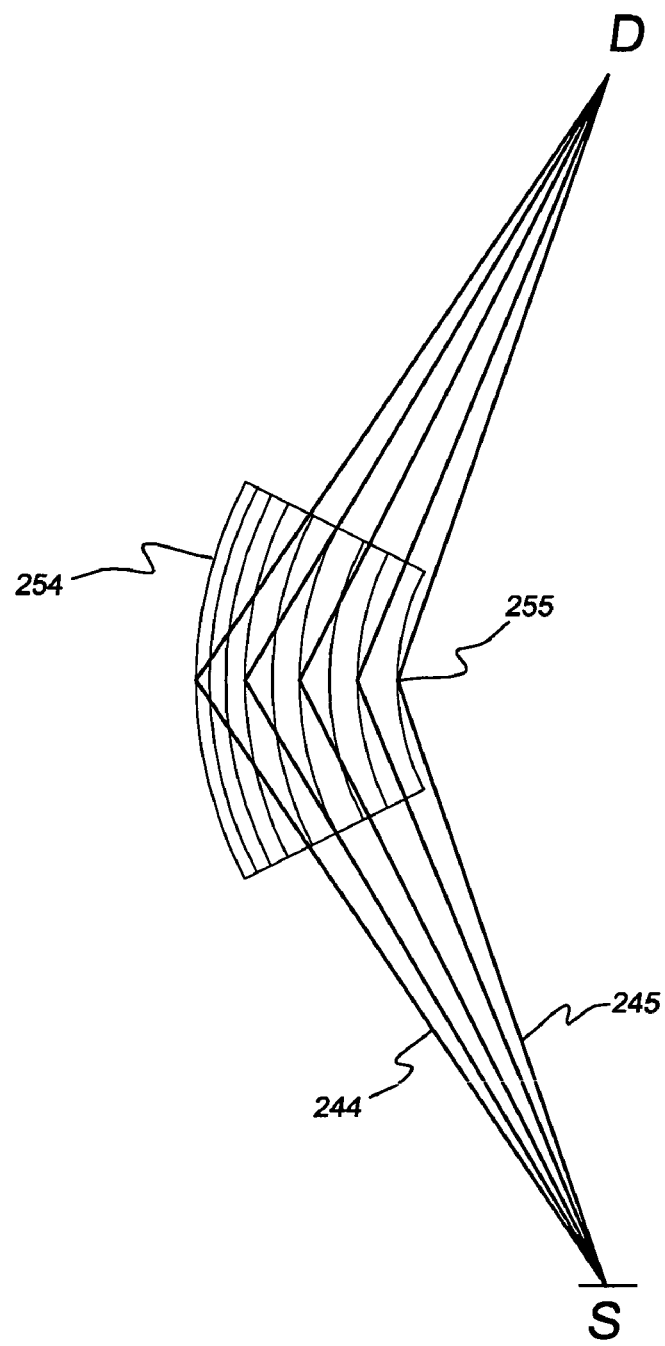
FIG. 6 illustrates the focusing effect by a mechanically bent crystal in Laue Diffraction, in accordance with features of the present invention.

The second kind of focusing that occurs in curved diffraction crystals results from the distortion of the crystalline planes due to the bending. The convex side of the crystal is stretched, while the concave side is compressed. The stretching causes the spacing between crystalline planes to decrease, while the compression causes the spacing to increase. This produces a uniform gradient in the spacing as a function of radial position. This gradient can compensate for the change in angle of the incident gamma rays in the radial direction and generate Laue focusing. This focusing is illustrated in FIG. 6. Again, the gamma ray passes through the crystal until it encounters crystalline planes with the right Bragg angle and is then diffracted. Because the crystalline planes are curved, the gamma ray will not encounter any further planes at the right Bragg angle so it will leave the crystal in the diffracted beam. The variation in the Bragg angle due to the variation in the spacing of the planes also results in the focusing at the detector of a broader cone of photons emanating from the source. As shown in FIG. 6 all the photons emanating from the source S between the angle 244, equal to the Bragg angle near the convex face 254, and the angle 245, equal to the Bragg angle near the concave face 255, are focused at one point D on the detector. One can achieve diffraction efficiencies approaching 100 percent in this arrangement. Again, the only loss is from atomic absorption. Again, a point source generates a narrow line image on the detector. The ideal radius of curvature, r(Laue) is given by r(Laue)=(S/sin p)× (Poisson's Ratio)=r(Bragg)×Poisson's Ratio.

Figure 7:
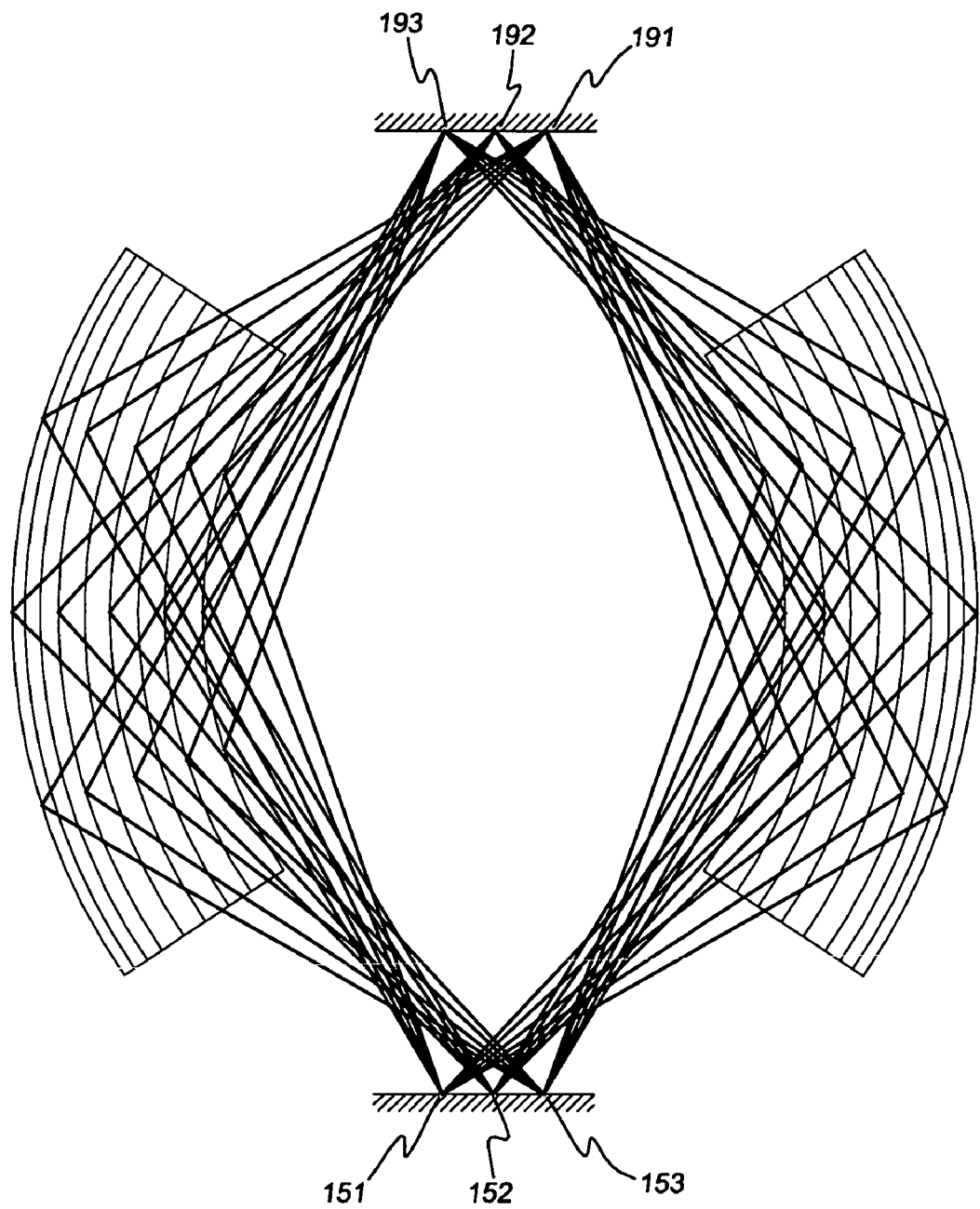
FIG. 7 illustrates the focusing effect of an extended source by a mechanically bent crystal in Laue Diffraction, in accordance with features of the present invention.

Poisson's ratio for crystals fall in the range of 0.2 to 0.5, thus the ideal radius for Laue focusing is smaller than for Bragg focusing, resulting in a greater curvature for the Laue focusing. The width of the source that the Bragg focusing can cover is limited by the radial size of the crystal. In Laue focusing the width of the source that can be focused is controlled by the total curvature of the crystal and can be much larger than for Bragg focusing. In practice for any arbitrary curvature the gamma ray passes through the crystal until it encounters a region where the Bragg angle is correct for diffraction and then is diffracted with a focusing properties that are a combination of the two types of focusing depending on the radius of curvature. As shown in FIG. 7, the variation in the Bragg angle due to the variation in the spacing of the planes also results in the focusing at the detector of a broad region of the source. Note that in FIG. 7 three source points 151, 152, and 153 are imaged onto separate detector points 191, 192, 193 respectively.

Lens Design Detail

The first step in determining the material and orientation of the diffracting crystals is to select the energy of the radiation that will be observed and the focal length F of the focusing means 18 one wants to achieve. In the simplest embodiment of the invention, a single lens is utilized, in a lens/detector array 17, but a lens/detector assembly 17 having a plurality of lenses is also suitable.

Where lenses of focal length F1, F2, F3, etc. . . . are placed in close proximity or contact with each-other, the focal length of the combination is given by equations 2 through 6.

Equation 2 gives the focal length for one lens, where p is the Bragg angle used in the lens and R is the radius of the crystal ring 45 (FIG. 7).

$$F = R/(\tan 2p) \quad \text{Eq. 2}$$

Equation 3 gives the focal length for two lenses, where $p_1$ and $p_2$ are the Bragg angles used in the first and second lenses and R1 and R2 are the radii used in the first and second lens, respectively.

$$F12 = (R1-R2)/\tan 2p_1 + R2/\tan(2p_1 + 2p_2) \quad \text{Eq. 3}$$

Equation 4 gives the focal length for three lenses, where $p_1$, $p_2$ and $p_3$ are the Bragg angles used in the first and second and third lenses and R1, R2 and R3 are the radii used in the first, second and third lenses, respectively.

$$F123 = (R1-R2)/\tan 2p_1 + (R2-R3)/\tan 2(p_1+p_2) + R3/\tan 2(p_1+p_2+p_3) \quad \text{Eq. 4}$$

If the lenses are very close together, then the R's become approximately equal and the approximate formula for the focal length is given by equation 5.

$$F12 \ldots n = R(\text{Ave})/\tan 2(p_1+p_2+p_3 \ldots p_n) \quad \text{Eq. 5}$$

If all of the Bragg angles are quite small, the focal length can be approximated by equation 6:

$$1/(F12 \ldots n) = 1/F1 + 1/F2 + \ldots + 1/Fn \quad \text{Eq. 6}$$

The set of atomic layers to be used for each ring 45 is determined by the condition that all the rings must have the same focal length F. For rays near the lens axis (small p) the relation between lens-source distance S, lens-detector distance D, and focal length F is given approximately by equation 7.

$$(1/F) = (1/S) + (1/D) \quad \text{Eq. 7}$$

In practice S and D as shown in FIG. 3 are both chosen to be 2F, then the Bragg angle p is arctan[R/(2F)] where R is the radius of the ring.

The Bragg condition yields the relation between the ring radius, focal length, radiation wavelength λ and atomic layer spacing d, given by equation (8).

$$R/F = \tan[2 \arcsin(\lambda/2d_{hkl})] \quad \text{Eq. 8}$$

For F>>R, i.e., for small angles, Equation 8 yields $$d_{hkl} = \lambda F/R \quad \text{Eq. 9}$$

In practice, a gamma ray with a specific energy (and therefore wavelength λ) is selected. Then, the crystalline plane spacings of an available crystal are tabulated. This information is combined with the desired focal length F to arrive at the respective radii R for the crystal rings, pursuant to equation 10:

$$R = d_{hkl}/\lambda F \quad \text{Eq. 10}$$

Finally, the size of the crystals is chosen.

(Alternately, λ is determined from the desired gamma ray energy, then F is chosen, and the available values of $d_{hkl}$ are identified, so that the values of R for the rings are suitable).

Bent Crystal Manufacture Detail

Each crystal diffraction lens 18 utilizes a plurality of nearly perfect diffracting crystals, where nearly perfect denotes high-quality grade commercially available crystals. Possible crystalline materials include, but are not limited to, silicon, quartz, tin, molybdenum, germanium, silver, gold, and copper. (Germanium, Silicon, Copper and Quartz have been found by the applicant to be suitable for the fabrication of x-ray and gamma-ray lenses for energies of around 150 keV.) The present invention provides a six-step method for repeatable, accurate, and economical production of thousands of bent crystal elements of the desired thickness and curvature.

The optimum radius of curvature for the Bragg focusing is given by: radius(Bragg) r(B)=distance from the source to the crystal lens (S) divided by the sine of the Bragg angle p, or r(B)=S/sin p.

The optimum radius for the Laue focusing is given by radius(Laue) r(L)=radius(Bragg)×Poisson's Ratio P for the crystalline planes being used.

Since Poisson's Ratio in silicon and many other crystals tends to be in the range of 0.2 to 0.5, the desired radius for Laue focusing tends to be 2 to 5 times smaller than the desired radius for Bragg focusing. Thus the actual radius used in the crystal element will be a compromise between these two radii, depending on the desired characteristics of the lens. (Poisson's Ration for the [111] planes in silicon is 0.358, thus the ideal radius for Laue focusing is 2.8 times smaller that the ideal radius for Bragg focusing.) It is the presence of the Laue focusing that makes it relatively easy to obtain spatial resolution that is smaller than the radial dimensions of the crystal elements. Because in the present invention the spatial resolution is not limited by the angle subtended by the radial thickness of the crystal element, one can use shorter source-lens distances than heretofore without loss of sensitivity and resolution. With a shorter source-lens distances, one obtains a shorter focal length systems.

The dimensions of the individual elements will vary depending of the desired characteristics of the lens. Typical dimensions could be 0.8 mm radial thickness, 20 mm length in the direction of the photon beam, and 2.5 mm wide. (See FIG. 6) Depending on the desired characteristics of the lens the radial thickness could be anywhere from 0.1 mm to 10 mm. The actual thickness being governed by the radius of the bend desired in the crystal. The dimensions of the length will also vary from a few mm to 10 or 20 cm or larger depending on the size of the lens. As the length of the crystal elements is increased the solid angle of the lens that sees the incident gamma rays is increased. This increases the efficiency of the lens. With a careful design the solid angle can match 80 percent of the area of the lens. The width of the crystals will vary from as small as 0.1 mm to a few cm, depending on the size of the lens and the desired resolution of the lens.

First, single crystal silicon (or other appropriate crystal material) plates of the desired thickness (from 0.1 mm to 10 mm depending on the crystal's brittleness, desired resolution, and bending radius) and of the appropriate Miller indices orientation depending on the wavelength of the radiation are cut from perfect or nearly perfect single crystal boules or cylinders with an axis orientation perpendicular to the desired planes for short crystals and an axis parallel to the crystalline planes for long crystals. Then these plates are lapped and polished in the customary manner.

Secondly, a set of two or more plates (or a plurality of sets side by side) is selected and the plates are contacted with glue between each layer and then either pressed or passed through a rolling apparatus to ensure a uniform glue thickness. (The glue must be such that it hardens only when activated by heat or other means.) Then the set is placed in a bending apparatus. This apparatus may be a four-point bender or one where the plates are pressed against a curved surface, so that the set is bent to the appropriate radius. The most accurate method is pressing against a curved surface. The curved surface often has a large radius, 5 to 100 m. This radius must be very uniform for the crystals to perform properly. These very precisely curved surfaces are made by first making the surface of an appropriately size block very flat and the applying a variable thickness coating to the surface that has the desired shape and thickness. Often the rise in the center of this curved surface will only be a few microns, so the curve needs to be accurate to a few hundredths of a micron. This variable thickness coating can be applied through selective evaporation techniques. The bending apparatus allows in-situ measurements so that one may check the curvature of the plates by optical or mechanical means. Frequently, one cannot bend a crystal into a pure cylindrical arc. This latter bending produces a deformation of the crystal in a direction orthogonal to the originally desired arc, so that one obtains a surface with two finite and approximately orthogonal planes of curvature. These planes of curvature and the associated radii can be controlled if one forms sets of dissimilar plates, choosing plates with different but appropriate orientations to form a set with bent crystal with tailored bending radii. The ideal shape of the bent crystals for magnifying lenses is ellipsoidal rather than cylindrical. Bent crystals with an ellipsoid like shape can be made with the same ease as ones with a cylindrical shape. Also, one can fashion hyperbolic, parabolic, and other shapes. One or more of the plates may be a non-crystalline material that provides rigidity to the set once it is bent.

Figure 9:
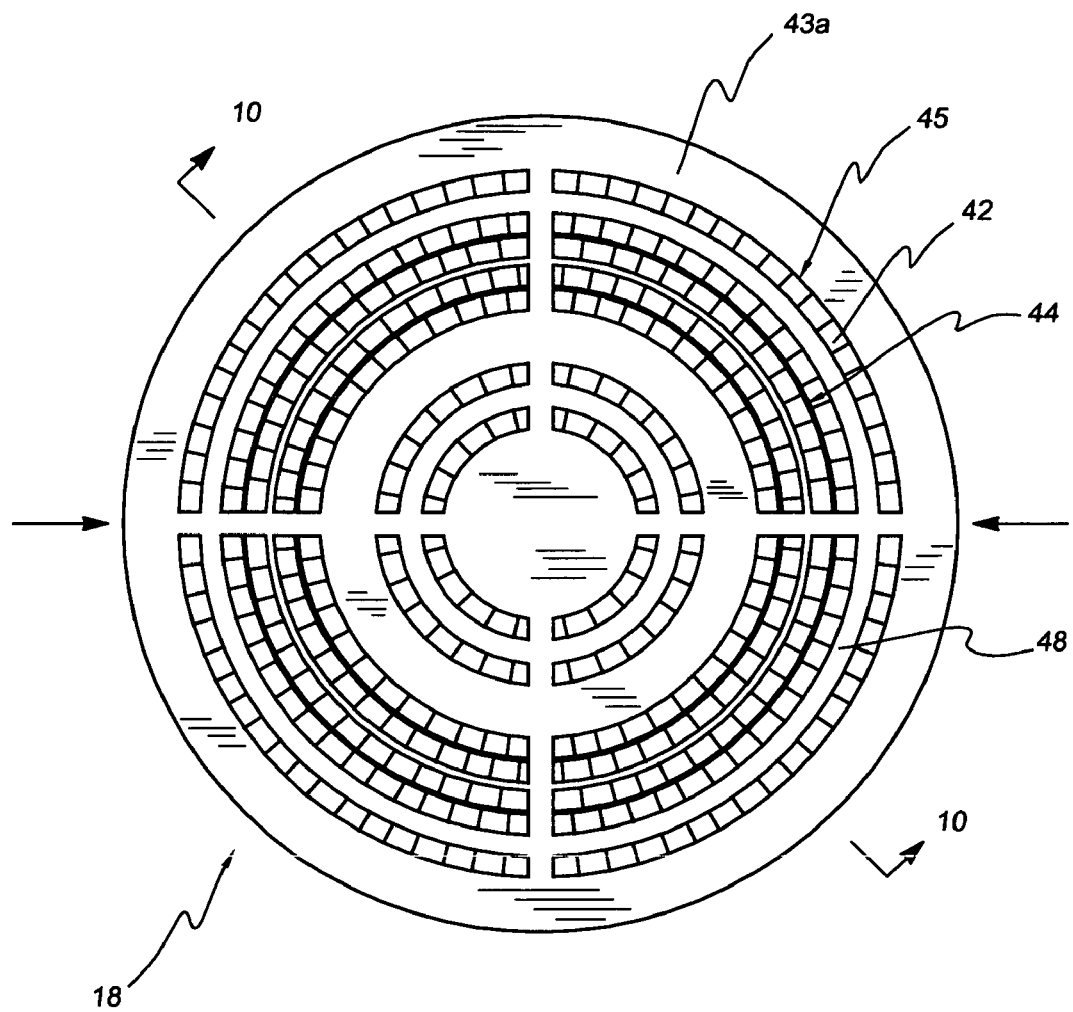
FIG. 9 is a plan view of a crystal diffraction lens, in accordance with features of the present invention.

Third, while the set of plates is in the bending apparatus, the glue is activated by such means as heat or ultraviolet light. FIG. 9 shows two bent crystal elements cemented together into a crystal element 42 with the face 59 of the crystal set being the face through which the radiation enters the crystals.

Fourth, the set is released from the bending apparatus and the radius is re-measured. Any deviation from the target radius at this step or future steps (due, for example, to the so-called spring back) must be detected and compensated for.

Fifth, a number of such sets are placed on top of each other, with or without a separating layer such as wax, and then this assembly placed into a holder.

Finally, sixth, the assembly is then cut, preferably in electron discharge machine (EDM) first in one and then in the orthogonal direction to produce a large number of smaller rectangular composite bent crystals of the desired shape, size, and orientation.

This process (with variations obvious to persons skilled the art) can produce thousands of sets economically, reliably, and consistently. Such variables as crystal plate thickness, an additional backing plate, or the application of unequal moments can produce a variety of crystal profiles, including elliptical or parabolic profiles. This process can be employed for the production of bent diffracting crystals for a variety of non-lens connected applications.

The same method can be used for any crystal diffraction apparatus where the wavelength of the photon, neutron, electron or other particles is comparable to the spacing of the crystal layers.

Diffraction Lens Construction.

Each crystal element needs to be placed at the right radial distance and with the right orientation (Bragg angle) in the lens frame. Thus the lens frame needs to allow one to adjust the Bragg angle while holding the radial distance constant. This is best done by supporting the crystal elements at two points in the photon diffraction plane. There many ways to generate a lens frame that supplies this kind of support. One example is the use of two identical thin plates with appropriate slots cut in them and appropriately spaced to support the different rings of crystals.

Figure 11:
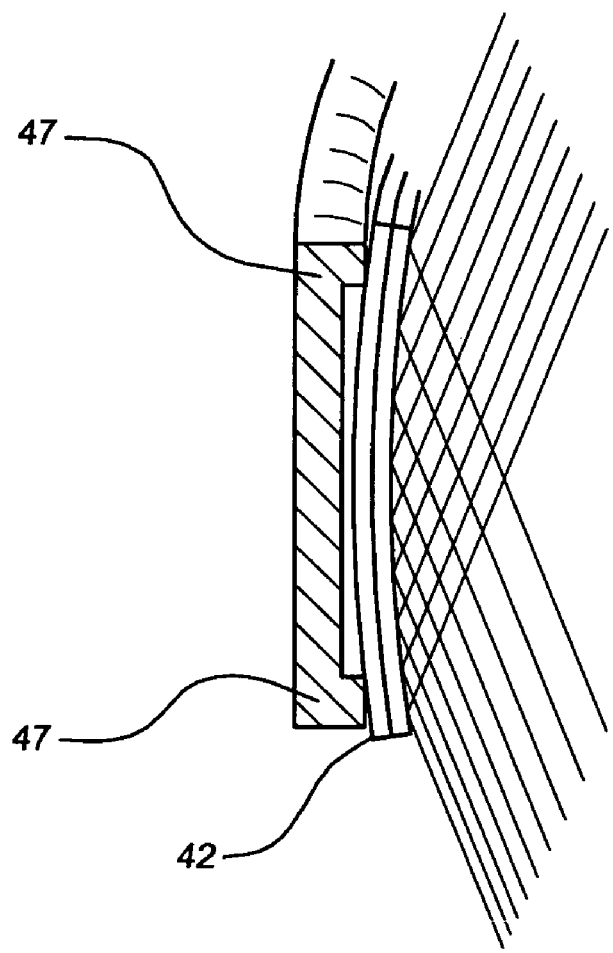
FIG. 11 is a schematic detail view of an alternate embodiment of a the assembly of a crystal diffraction lens, in accordance with features of the present invention of the method for constructing a Laue diffraction lens out of a plurality of diffracting crystals, in accordance with features of the present invention.

FIG. 9 is a view of FIG. 3a along lines 9-9 giving a frontal view of a typical embodiment of a lens 18, while FIG. 10 shows a cross section of the lens along line 10-10 of FIG. 9 for an exemplary embodiment of a lens 18. Each lens 18 comprises two parallel support plates 43a, 43b (See FIG. 10) but under certain circumstances, as shown in FIG. 11, a single plate with the appropriate raised ridges 47 may be used for each crystal ring. The plates 43a, 43b comprise a low atomic number metal such as aluminum, beryllium, or magnesium but other materials are suitable. This is done so that the gamma rays can pass through these plates without being attenuated to any significant degree. Regions of the surface of the plates 43 define a series of apertures arranged as concentric rings 45. Each ring contains a plurality of diffracting crystal arcs 42 of the same material, radius, and crystal plane orientation. The material and orientation are determined according to the procedure described supra.

For both Laue and Bragg diffraction, the diffracting crystals are mounted onto the plate in such a manner that once mounted, all the crystals in a given ring will be so oriented as to use the same set atomic layers to satisfy the Bragg condition. In a typical embodiment, the crystals in a given ring are all of the same material, orientation, and curvature but crystals in different rings may be of different materials, orientation, and curvature.

Mounting of the crystals 42 onto the plates 43a, 43b can occur in a variety of ways. One method is to attach the two thin plates together with appropriate spacers and mount the frame in a rotating frame. A radioactive source of the energy to be focused is placed so that its radiation will be diffracted the crystals in one of the rings. A crystal is then placed in the lens frame and its diffracted beam is measured by an appropriately positioned detector. Slight adjustments are made to the position of the bent crystal in the lens frame by sliding in and out of the frame parallel to the axis of the lens until the best focus is obtained for that crystal element. When this is achieved the crystal element is glued in place. The lens frame is then rotated so that a new crystal element can be placed in the lens frame and tested in a similar manner. This procedure is repeated in this ring and in subsequent rings until the lens is completely filled with crystals. Only one crystal element is exposed to the radiation at a time through an appropriate shield. When this shield is removed it is possible to test the performance of the whole lens at any time during the assembly. Different rings may be used to focus sources of different energies.

For very small diameter lenses, the lens frame may be replaced by thin spacers between the crystal element in adjacent rings.

Scanning a Source and Formation of an Image

The lens detector assembly achieves its best performance for sources located on or very near the axis of the assembly. When the source 15 is not situated on the axis of the assembly, the movable platform 16 is advanced until the source is positioned on the axis of the assembly.

A straightforward method of source detection and imaging is scanning the relevant area. This is almost always necessary as a first step unless a possible source location has been determined by a previous scan or through another type of imaging system. In order to scan across the source 15, one may change the position of the body 12 using the means provided for moving the table 16. Alternatively, one may change the orientation of the lens/detector assemblies and adjust the source/lens and lens/detector distances as indicated by Equation 3 by means of the tracks 22 on which lenses and detectors are mounted. In yet another alternative, one can move the whole lens system relative to the source.

Also, equation 5 shows the focal length's dependence on the wavelength of the radiation. The lens 18 and detector 19 are mounted on tracks 22 allowing the use of a given lens to detect radiation of a different wavelength by adjusting the lens-source and lens-detector distances as dictated by equation 3. Electronic sensors are mounted on tracks 22 and their signals are recorded and analyzed by the computer. For gamma rays with energies in the 150 keV range the focal length is proportional to the energy. Thus to focus a different energy one only needs to change the distance from the source to the detector and similarly, the distance from the lens to the detector. As long as the sine of the Bragg angle is close to the value of the tangent of the Bragg angle, this change in distances will result in a near perfect focus of the new energy radiation.

Instead of relying on tracks 22, imaging of radiation of different wavelengths can also be accomplished by using different lenses, and keeping the elements of the assembly stationary. For example, a source having a first energy can be scanned in toto by moving the table 16 with respect to the center of the lens/detector arrays (see FIG. 1). If the device is to be used for gamma rays of a second energy, one can construct a plurality of different lenses using crystals with atomic spacings so chosen that one obtains the same focal length as the lenses used to focus the first source.

Signals from the detector arrays 19 are analyzed by a computer in conjunction with the data from the detectors 20 and those from the sensors on the movable platform 16 and the lens and detector tracks 22.

Device Apertures

Figure 13:
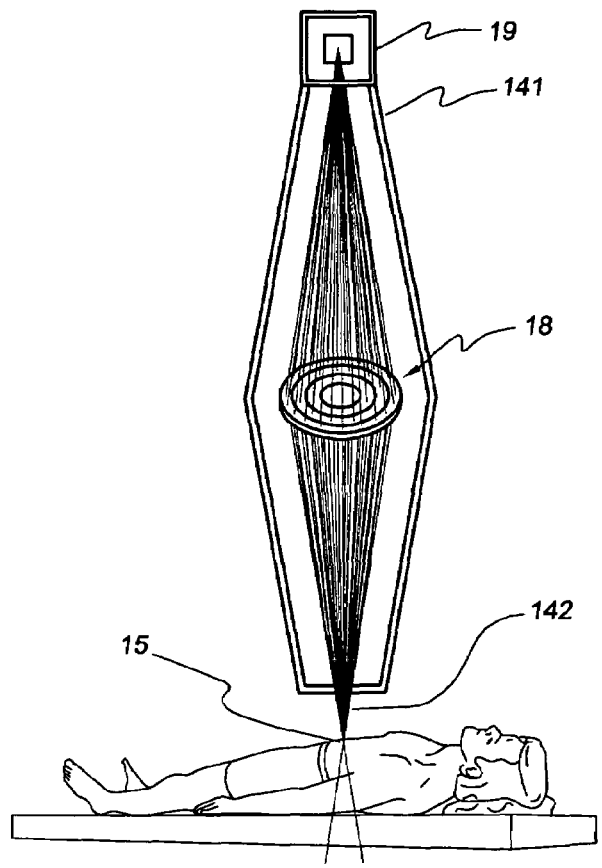
FIG. 13 illustrates the combined effect of narrow apertures in front of the detector array and in front of the source, in accordance with features of the present invention.

Restricting the area of the apertures in front of the detector array and in front of the source improves significantly the spatial resolution of the device when the latter is used in a scan mode. As shown in FIGS. 12a and 12b, a decrease in the detector array aperture 140 reduces the field of view, i.e. the area 196 of the source 15 that can be viewed at any one time. Restriction of the detector aperture also reduces the background seen by the detector array. Restriction of the source aperture 142 has a similar advantage in reducing the apparent size of the area viewed by the lens and in reducing the background radiation reaching the detector array. FIG. 13 illustrates the combined effect of narrow apertures in front of the detector array and in front of the source. This approach can reduce the background counting rate significantly.

It is advisable that the size and position of the apertures be adjustable so that one may adapt the device to the specific requirements for a given observation.

Use of a Multi-component Detector Array

Figure 14:
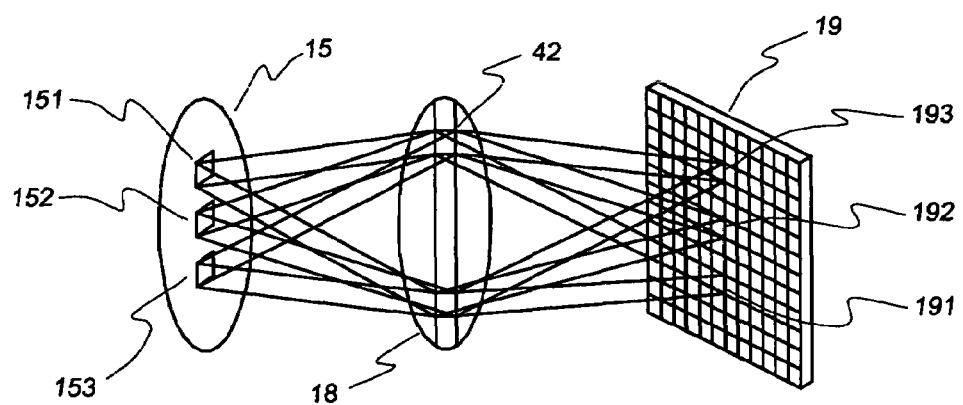
FIG. 14 illustrates the effect of a many-elements detector array in accordance with features of the present invention.

FIG. 14 depicts an alternate embodiment of the invention where using a many-component detector array presents the same spatial resolution advantages as the restriction of the detector aperture. In this case each pixel in the detector acts like a separate small aperture, allows one to take data in each aperture simultaneously. This approach avoids the loss of count rate that occurred with the use of a single aperture in front of the detector as mentioned above. FIG. 17 shows how points 151, 152, and 153 are imaged onto separate detectors 191, 192, 193. Such an array has obvious advantages in that it reduces the time necessary to acquire the necessary data. For instance, a 1 cm square array of 1 mm by 1 mm detectors produces a high spatial resolution (1 mm) life size image of a 1 cm object such as a tumor without having to scan the object.

One Shot Imaging of an Extended Source.

Figure 8:
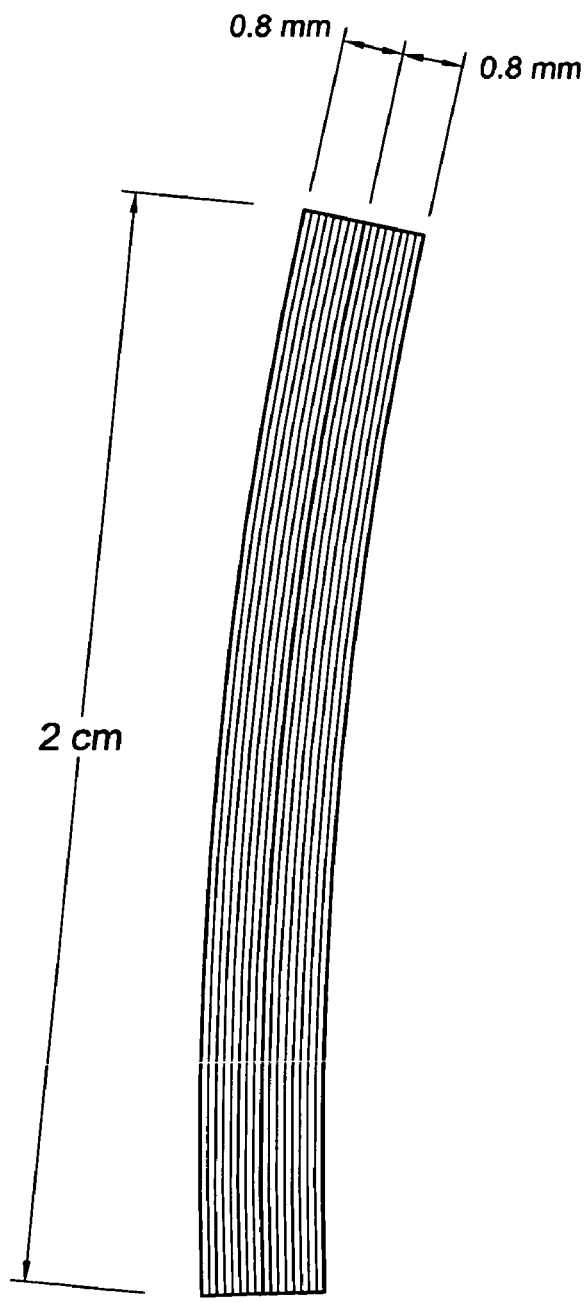
FIG. 8 is a profile view of two crystal strips cemented together, in accordance with features of the present invention.

FIG. 7 shows the that a bent crystal element focuses gamma rays from separate source points to separate points on the detector. This effect is enhanced with a multi-plate element. (See FIG. 8) This generates a real and inverted image of the source on the detector and this with very high resolution. All the crystal elements on the lens may be set so that one has the x-ray and gamma-ray equivalent of an optical positive focal length (convex) lens generating a real and inverted image of a source on a detector If one is imaging the 140.5 keV gamma ray from Tc99m, then the maximum attenuation in a silicon crystal that is 2 cm long will be 22 percent. Theoretically any size source can be imaged at the detector to within a few percent of its actual size with bent crystals. This is quite different than with unbent crystals where one must use mosaic crystals to achieve reasonable sensitivities. With unbent crystals the resolution is limited to 1.6 times the radial thickness of the crystal element. The factor of 1.6 comes from the structure of the circular lens structure. With the bent crystal lens using perfect Laue focusing the resolution could be as small as 10 microns.

The fact that the invented lens resembles a simple optical convex lens and has the capability of forming a magnified image of the source. (see FIG. 3b) confers special advantages. The magnified image makes a pixel detector more useful, in that the pixels will not have to be as small for the same resolution. A 1 mm×1 mm pixel can contain the energy from a 140.5 keV gamma ray from Tc99m, but a 0.1 mm×0.1 mm pixel is too small to contain the x-ray that is produced in the photoelectric absorption of the gamma ray or the Compton scattered gamma ray produced in a Compton event. In principle one could build a lens with a magnification of 8. This would magnify a 0.1 mm source to 0.8 mm at the detector and make the pixel detector efficient. The field of view of the lens without any scanning could be 2 to 3 mm in diameter giving and image at the detector with a spatial resolution of 0.1 mm over a 2 to 3 mm diameter area. With scanning this area could be expanded as much as one needed.

The ability of reduce the size of the lens without losing efficiency or resolution, and in fact improving both of them combined with the understanding that one can now consider spatial resolution of 0.1 mm, suggests that one should consider using the power of the lens to magnify the image, just as one can use a simple convex lens for visible light can be used to magnify a light image. This will solve the pixel detector problem in that a magnified image can use large pixels for the same resolution. A 1 mm×1 mm pixel can contain the energy from a 140.5 keV gamma ray from Tc99m, but a 0.1 mm×0.1 mm pixel is too small to contain the x-ray that is produced in the photoelectric absorption of the gamma ray or the Compton scattered gamma ray produced in a Compton event.

If one were to use magnification with the copper lens disclosed in U.S. Pat. No. 5,869,841 (1999), with a focal length of 50 cm and a distance from source to detector of 200 cm, a magnification of a factor of 2 would increase this source to detector distance to 225 cm and a magnification of a factor of 4, would increase the source to detector distance to 312.5 cm, which is difficult to handle. A reduction in the focal length of the prior art lens by a factor of 4 with a similar reduction in the size of crystal elements to a radial width of 1 mm, would reduce the source to detector distance to 56.3 cm (see FIG. 20) and generate an image on the detector of a point source of 2 to 3 mm in diameter. Magnification of this image would not improve the resolution. Thus one can see the advantages of going over to bent crystal lenses where the resolution can be as small as 0.1 mm.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for high spatial resolution imaging of x-ray and gamma radiation comprising:
   a) supplying one or more sources of radiation;
   b) focusing said radiation onto one or more detectors by means of mechanically bent diffracting crystals, wherein each source has a first size and wherein the radiation emanating from said source is focused onto a detector area four times larger than said first size;
   c) analyzing said focused radiation to collect data as to the type and location of the radiation; and
   d) producing an image using the data wherein said image is produced by an array of detectors.

2. A method for high spatial resolution imaging of x-ray and gamma radiation comprising:
   a) supplying one or more sources of radiation;
   b) focusing said radiation onto one or more detectors by means of mechanically bent diffracting crystals;
   c) analyzing said focused radiation to collect data as to the type and location of the radiation; and
   d) producing an image using the data, wherein said source is a point source and said radiation is focused onto a detector area having a width of 0.3 mm.

3. The method as recited in claim 2 wherein an extended image having 0.3 mm resolution is produced from a 3 mm diameter source with said source, crystals, and detectors remaining stationary.

4. The method as recited in claim 2 wherein the mechanically-bent crystals are produced by a method which comprises:
   a) selecting a crystalline material and cutting from said material single crystal slabs of desired thickness and with Miller indices orientation determined according to the radiation to be focused;
   b) forming sets of two or more juxtaposed plates, at least one of which plates is one of said crystal slabs, by contacting said plates with an uniform layer of glue placed intermediate the plates, wherein said glue hardens only when it is activated;
   c) bending to a predetermined curvature one or more of said sets by means of a bending apparatus that allows in-situ measurements of the curvature of the plates;
   d) activating said glue while the set of plates is in the bending apparatus;
   e) releasing said set from the bending apparatus.

5. The method as recited in claim 4 wherein at least two of said crystal slabs in a said set are chosen to be dissimilar.

6. A device for high spatial resolution imaging of a plurality of sources of x-ray and gamma-ray radiation comprising:
   a) a means for locating the sources of radiation;
   b) a plurality of mechanically bent diffracting crystals of a width not exceeding the resolution for focusing radiation emanating from the located sources and directing it to a plurality of detectors;
   c) detector arrays for analyzing said directed radiation to collect data as to the type and location of the source of the radiation wherein each source has a first size and wherein the radiation emanating from said source is focused onto a detector area four times larger than said first size; and
   d) a means for converting the data to an image.

7. The device as recited in claim 6 wherein the diffracting crystals form a plurality of lenses.

8. The device as recited in claim 7 wherein each lens comprises a plate defining apertures arranged as concentric rings, and wherein the crystals are oriented within the apertures so as to diffract radiation of a predetermined energy to the same focal point.

9. The device as recited in claim 7 wherein said lenses have a focal length of 0.25 meters or less.

10. The device as recited in claim 6 wherein said bent crystals have lattice planes with a continuously variable lattice spacing.

11. A device for high spatial resolution imaging of a plurality of sources of x-ray and gamma-ray radiation comprising:
    a) a means for locating the sources of radiation;
    b) a plurality of mechanically bent diffracting crystals of a width not exceeding the resolution for focusing radiation emanating from the located sources and directing it to a plurality of detectors;
    c) detector arrays for analyzing said directed radiation to collect data as to the type and location of the source of the radiation wherein said detectors in said detector arrays have a resolution of 0.3 mm or less; and
    d) a means for converting the data to an image.

12. A method for bending crystals for use in a crystal diffraction system comprising:
    a) selecting a crystalline material and cutting single crystal slabs with pre-determined Miller indices orientation and of desired thickness from large single crystals;
    b) forming sets of two or more juxtaposed plates, said plates comprising one or more of said slabs, by contacting said plates with an uniform layer of glue placed intermediate said plates, wherein said glue hardens only when it is activated;
    c) bending to a predetermined curvature one or more of said sets by means of a bending apparatus that allows in-situ measurements of the curvature of the plates;
    d) activating said glue while the set of plates is in the bending apparatus; and
    e) releasing said set from the bending apparatus.

13. The method as recited in claim 12 wherein at least two of said crystal slabs in a said set are chosen to be dissimilar.

* * * * *